(12) United States Patent
Good et al.

(10) Patent No.: US 8,064,998 B2
(45) Date of Patent: Nov. 22, 2011

(54) HEART STIMULATING SYSTEM

(75) Inventors: Xin Good, Tigard, OR (US); David F. Hastings, Lake Oswego, OR (US); Hannes Kraetschmer, West Linn, OR (US); Dirk Muessig, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 1089 days.

(21) Appl. No.: 11/863,375

(22) Filed: Sep. 28, 2007

(65) Prior Publication Data
US 2009/0088814 A1 Apr. 2, 2009

(51) Int. Cl.
*A61N 1/00* (2006.01)
(52) U.S. Cl. ............................................. 607/9
(58) Field of Classification Search ................ 607/9, 16, 607/25, 27
See application file for complete search history.

(56) References Cited

U.S. PATENT DOCUMENTS
| | | | |
|---|---|---|---|
| 4,513,743 A | 4/1985 | Van Arragon |
| 5,372,607 A | 12/1994 | Stone et al. |
| 6,925,326 B1 | 8/2005 | Levine et al. |

OTHER PUBLICATIONS

European Search Report, dated Feb. 4, 2009.

*Primary Examiner* — Eric D. Bertram
*Assistant Examiner* — Elizabeth K So
(74) *Attorney, Agent, or Firm* — Arc IP Law, PC; Joseph J. Mayo

(57) ABSTRACT

Heart stimulating system for stimulating at least a ventricle of a heart including: stimulation pulse generator adapted to generate stimulation pulses and connected to a ventricular stimulation electrode for delivering stimulation pulses, atrial sensing stage connected to an electrode for picking up potentials inside an atrium and adapted to sense an excitation or contraction of atrial myocardium, ventricular sensing stage connected to an electrode for picking up potentials inside a ventricle and adapted to sense an excitation or contraction of ventricular myocardium, memory for AV-delay values, a control unit adapted to trigger said stimulation pulse generator to generate ventricular stimulation pulses timed based on AV-delay values stored in said memory and to acquire atrioventricular interval samples, and atrioventricular interval timing analyzing unit for receiving atrioventricular interval samples from said control unit and adapted to generate at least one histogram based on said atrioventricular interval samples and analyze said histograms.

23 Claims, 2 Drawing Sheets

HEART STIMULATING SYSTEM

BACKGROUND OF THE INVENTION

1. Field of the Invention

The invention refers to a heart stimulation system for stimulating at least one chamber of a heart by means of electrical stimulation pulses that are delivered when a delay time started by a cardiac event expires. The invention particularly refers to implantable medical devices such as implantable pacemakers and implantable cardioverter/defibrillators for atrial synchronous stimulation of a ventricle of a heart.

2. Description of the Related Art

Implantable heart stimulators can be used for cardiac rhythm management (CRM) for treating a variety of heart functional and rhythm disorders including but not limited to bradycardia, tachycardia or fibrillation by way of electric stimulation pulses delivered to the heart tissue, the myocardium. A sufficiently strong stimulation pulse outside a heart chamber's refractory period leads to excitation of the myocardium of that heart chamber, which in turn is followed by a contraction of the respective heart chamber.

Depending on the disorder to be treated, such heart stimulator generates electrical stimulation pulses that are delivered to the heart tissue (myocardium) of a respective heart chamber according to an adequate timing regime. Delivery of stimulation pulses to the myocardium is usually achieved by means of an electrode lead that is electrically connected to a stimulation pulse generator inside a heart stimulator's housing and that carries a stimulation electrode in the region of its distal end. A stimulation pulse also is called a pace. Similarly, pacing a heart chamber means stimulating a heart chamber by delivery of a stimulation pulse.

In order to be able to sense the contraction a heart chamber which occurs naturally without artificial stimulation and which is called an intrinsic contraction, the heart stimulator usually includes at least one sensing stage that is connected to a sensing electrode and said electrode is placed in or near the heart chamber. An intrinsic excitation of a heart chamber results in characteristic electrical potentials that can be picked up via the sensing electrode and that can be evaluated by the sensing stage in order to determine whether an intrinsic excitation—called: intrinsic event—has occurred.

Usually, a heart stimulator features separate stimulation pulse generators for each heart chamber to be stimulated. Therefore, in a dual chamber pacemaker, usually an atrial and a ventricular stimulation pulse generator for generating atrial and ventricular stimulation pulses are provided. Delivery of an atrial or a ventricular stimulation pulse causing an artificial excitation of the atrium or the ventricle, respectively, is called an atrial stimulation event $A_P$ (atrial paced event) or a ventricular stimulation event $V_P$ (ventricular paced event), respectively.

Similarly, common heart stimulators feature separate sensing stages for each heart chamber to be of interest. In a dual chamber pacemaker usually two separate sensing stages, an atrial sensing stage and a ventricular sensing stage, are provided that are capable to detect intrinsic atrial events $A_S$ (atrial sensed event) or intrinsic ventricular events $V_S$ (ventricular sensed event), respectively.

As known in the art, separate sensing and pacing stages are provided for three-chamber (right atrium RA, right ventricle RV, left ventricle LV) or four-chamber (right atrium RA, left atrium LA, right ventricle RV, left ventricle LV) pacemakers or ICDs.

By means of a sensing stage for a heart chamber to be stimulated, the pacemaker is able to only trigger stimulation pulses when needed that is when no intrinsic excitation of the heart chamber occurs in the allotted time. Such mode of pacing a heart chamber is called demand mode. In the demand mode the pacemaker schedules an atrial or a ventricular escape interval that causes triggering of an atrial or ventricular stimulation pulse when the escape interval times out. Otherwise, if an intrinsic atrial or ventricular event is detected prior to time out of the respective atrial or ventricular escape interval, triggering of the atrial or ventricular stimulation pulse is inhibited. Such intrinsic (natural, non-stimulated) excitations are manifested by the occurrence of recognizable electrical signals that accompany the excitation and depolarization of a cardiac muscle tissue (myocardium). The depolarization of the myocardium is usually immediately followed by a cardiac contraction. For the purpose of the present application, depolarization and contraction may be considered tightly coupled events and the terms "depolarization" and "contraction" are used herein as synonyms.

In a heart cycle, an excitation of the myocardium leads to a depolarization of the myocardium that leads to a contraction of the heart chamber. If the myocardium is fully depolarized it is unsusceptible for further excitation and is thus refractory. Thereafter, the myocardium repolarizes and thus relaxes and the heart chamber expands again. In a typical intracardiac electrogram (iEGM) depolarization of the ventricle corresponds to a signal known as the "R-wave". The repolarization of the ventricular myocardium coincides with a signal known as the "T-wave". Atrial depolarization is manifested by a signal known as the "P-wave".

A natural contraction of a heart chamber can be similarly detected by the evaluating electrical signals sensed by the sensing channels. In the sensed electrical signal the depolarization of an atrium muscle tissue is manifested by occurrence of a P-wave. Similarly, the depolarization of ventricular muscle tissue is manifested by the occurrence of a R-wave. The detection of a P-wave or a R-wave signifies the occurrence of intrinsic atrial, As, or ventricular, Vs events, respectively.

Several modes of operation are available in state of the art multimode cardiac stimulation systems. The modes of operation are concerned with which chambers of the heart are monitored for native activity; which chambers of the heart are provided with pacing therapy; and which cardiac functions are treated: inter-chamber conduction (AV Node, nodal disease); chronotropy (sinus node, sinus disease); and intrachamber conduction (bundle branch delays and blocks, conduction disorders). The operational modes of a stimulation system, single, dual or multi-chamber devices, are classified using a standard descriptive code. This invention covers the automatic characterization and determination of the timing objectives for managing inter-chamber and intra-chamber disorders.

The NBG code system is used to describe these modes of operations. In such a code, the first three letters describe the primary configuration. The First letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters, and wherein an "O" indicates no sensing occurs. The third letter of the code identifies the action or response that is taken by the pacemaker. In general, three types of action or responses are recognized: (1) an Inhibiting ("I") response wherein a stimulation pulse is delivered to the designated chamber at the conclusion of the appropriate escape interval unless cardiac activity is sensed during the escape interval, in which case the stimulation pulse is inhibited; (2) a Trigger ("T") response wherein a stimulation pulse to a prescribed chamber of the heart following a prescribed period of time after a sensed event; or (3) a Dual ("D") response wherein both the Inhibiting mode and Trigger mode may be evoked, e.g., with the "inhibiting" occurring in one chamber of the heart and the "triggering" in the other.

To the primary three-letter code, a fourth letter "R" may optionally be added to designate a rate-responsive pacemaker and/or whether the rate-responsive features of such a rate-responsive pacemaker are enabled ("O" typically being used to designate that rate-responsive operation has been disabled). A rate-responsive pacemaker is one wherein a specified parameter or combination of parameters, such as physical activity, the amount of oxygen in the blood, the temperature of the blood, etc., is sensed with an appropriate sensor and is used as a physiological indicator of what the pacing rate should be. When enabled, such rate-responsive pacemaker thus provides stimulation pulses that best meet the physiological demands of the patient.

To the fore mentioned first 4-letter code, a fifth code field may be added to designate the inter-chamber configuration.

A dual chamber pacemaker featuring an atrial and a ventricular sensing stage and an atrial and a ventricular stimulation pulse generator can be operated in a number of stimulation modes like VVI, wherein atrial sense events are ignored and no atrial stimulation pulses are generated, but only ventricular stimulation pulses are delivered in a demand mode, AAI, wherein ventricular sense events are ignored and no ventricular stimulation pulses are generated, but only atrial stimulation pulses are delivered in a demand mode, or DDD, wherein both, atrial and ventricular stimulation pulses are delivered in a demand mode. In such DDD mode of pacing, ventricular stimulation pulses can be generated in synchrony with sensed intrinsic atrial events and thus in synchrony with an intrinsic atrial rate, wherein a ventricular stimulation pulse is scheduled to follow an intrinsic atrial contraction after an appropriate atrioventricular delay (AV-delay; AVD), thereby maintaining the hemodynamic benefit of atrioventricular synchrony.

The AV-delay determines the chronological relation between an atrial event and a prescribed point of time of a ventricular event, the ventricular escape interval.

Since an optimal AV-delay may vary for different heart rates or stimulation rates and may even vary from patient to patient, the AV-delay usually is adjustable.

In order to promote natural ventricular events, often the ventricular escape interval is extended by a short time interval thus resulting in a prolonged ventricular escape interval called "AV hysteresis interval"

BRIEF SUMMARY OF THE INVENTION

It is an object of the invention to provide a heart stimulating system that provides for an appropriate yet simple setting of the AV-delay timing.

According to the present invention the object of the invention is achieved by a heart stimulator featuring:
a stimulation pulse generator adapted to generate electric stimulation pulses and being connected or being connectable to at least a ventricular stimulation electrode for delivering electric stimulation pulses to at least said ventricle of the heart,
a sensing stage connected or being connectable to an electrode for picking up electric potentials inside at least said ventricle of a heart, said sensing stage being adapted to sense an excitation or a contraction of a heart chamber,
a sensing stage connected or being connectable to an electrode for picking up electric potentials inside at least an atrium of a heart, said sensing stage being adapted to sense an excitation or a contraction of a heart chamber,
a memory for AV-delay values,
a control unit that is connected to said memory, said sensing stage and to said stimulation pulse generator, said control unit being adapted to trigger said stimulation pulse generator to generate ventricular stimulation pulses that are timed based on AV-delay values stored in said memory,
and an atrioventricular interval timing analyzing unit that is part of said control unit or that is connected to said control unit for receiving atrioventricular interval timing data from said control unit and that is adapted to
generate histograms based on said atrioventricular interval timing data received from said control unit and
analyze said histograms to determine at least one particular quantile atrioventricular interval that is a $m^{th}$ q-quantile of the atrioventricular interval distribution as manifested by the counts in said histograms.

Generally, quantiles are points taken at regular intervals from the cumulative distribution function of a random variable that in the present case is the cumulative distribution of the measured intrinsic atrioventricular conduction times. Dividing ordered atrioventricular interval data into q essentially equal-sized data subsets is the motivation for q-quantiles. The quantile points are the data values marking the boundaries between consecutive subsets. If the ordered atrioventricular interval data were divided into 100 essentially equal-sized data subsets (q=100), the boundaries between these subsets would be the percentile points (1 through 99). The median AV interval would be a member of the $50^{th}$ percentile; or the $m^{th}$ q-quantile with m=q/2. The $50^{th}$ percentile corresponds to the atrioventricular interval that is in the middle of the ordered sequence of atrioventricular intervals where one half of all recorded atrioventricular intervals are longer than the median atrioventricular interval and the other half is shorter than the median atrioventricular interval.

Preferably the atrioventricular interval timing analyzing unit is adapted to determine a specific $m^{th}$ q-quantile for a distribution of atrioventricular intervals. The $m^{th}$ quantile is the upper boundary of the subset, which includes the indicated AV interval. This subset includes the atrioventricular interval sample for which at least m/q (with 0<m<q) are shorter.

According to one preferred embodiment of the heart stimulating system the atrioventricular interval timing analysis unit is adapted to determine the median atrioventricular interval as defined above.

According to a further preferred embodiment of the heart stimulating system the atrioventricular interval timing analysis unit is adapted to determine an upper limit native atrioventricular conduction time, e.g. to the 97th percentile of at least a part of ordered recorded atrioventricular intervals.

The sensing stages, the stimulation pulse generators, the control unit and the memory for AV delay values are part of an implantable heart stimulator and are integrated into the heart stimulator's housing. The heart stimulator can be an implantable pacemaker or an implantable cardioverter/defibrillator or a combination of both.

The atrioventricular interval timing analyzing unit can be integrated into a housing of the implantable heart stimulator and can be a part of the unit.

Alternatively, the atrioventricular interval timing analyzing unit can be part of an external device that can be wirelessly connected to the implantable heart stimulator. The external device may be a patient device used for home monitoring purposes, or a central service center, that can be connected to the implantable heart stimulator via an external device next to the implantable heart stimulator or it can be a programmer used for wireless programming of the implantable heart stimulator. Making the atrioventricular interval timing analyzing unit part of an external device that eventually is connected to the implantable heart stimulator is a valid option, since it usually is sufficient to analyze atrioventricular conduction (AV conduction) and the duration of natural (intrinsic) atrioventricular intervals only from time to time. Thus higher order processing demanding adequate resources can easily be sourced out from the implantable heart stimulator to an external device.

Preferably, the atrioventricular interval timing analysis unit is further adapted to confirm sufficient atrioventricular conduction prior to generating a hysteresis AV delay value and not to generate a hysteresis AV delay value if no sufficient atrioventricular conduction is confirmed. In order to confirm sufficient atrioventricular conduction the atrioventricular interval timing analysis unit is preferably adapted to compare the number of intrinsic ventricular events Vs to the total number of ventricular events (Vs+Vp) within a predetermined time window. Preferably, sufficient atrioventricular conduction is confirmed if more than a specified minimal fraction (e.g. 3%) of all ventricular events are intrinsic events.

The object of the invention is achieved by a method for atrioventricular timing analysis and atrioventricular interval adjustment; said method comprises the steps of:
  acquisition of atrioventricular interval timing data,
  generation of histograms comprising bins wherein each bin is associated to dedicated range of atrioventricular intervals, and
  determination of at least one $m^{th}$ q-quantile atrioventricular interval.

Preferably, the $m^{th}$ q-quantile atrioventricular interval is a median atrioventricular interval.

In a preferred embodiment, the method includes the step of generating an AV-delay value to be said median atrioventricular interval minus a predetermined time interval, which compensates for the stimulation latency. The predetermined time interval preferably has a duration of 10 to 40 ms, e.g. 20 ms.

Similarly it is preferred that the method includes the step of generating an hysteresis AV delay value corresponding to the $m^{th}$ q-quantile atrioventricular interval with m being equal to or larger than 97% of q.

In a further preferred embodiment the method includes the steps of
  Accumulating and analyzing atrioventricular intervals recorded over at least 24-hr, using a long AV delay of 250 ms to 300 ms for ventricular stimulation.
  Checking for evidence of native (natural) atrioventricular conduction leading to intrinsic ventricular events Vs.
    If no evidence of native AV conduction is found, in particular if less than specified minimum fraction (e.g. 3%) of all recorded ventricular events are intrinsic ventricular events, then programming standard AV delay values into the AV delay memory and do not enable AV hysteresis
    If sufficient evidence of native AV conduction are found, in particular if equal to or more than a specified minimum fraction of (e.g. 3%) of all recorded ventricular events are intrinsic ventricular events, then determining a longer edge for the distributions of recorded atrioventricular intervals, e.g. the quantile that forms the upper threshold (e.g. $97^{th}$ percentile) of the recorded atrioventricular intervals, calculating the atrial sense latency time
    programming the hysteresis AV delay to include the longer edge of the distribution of recorded atrioventricular intervals, e.g. the 97-th percentile interval,
    programming a short ApVp delay as follows:
      preserving the AV hysteresis timing as constrained by the device's AV hysteresis options
      targeting the short AV delay to be shorter than the median ApVs interval by an amount equivalent to the stimulation latency, e.g. 20 ms.
      constraining the AV delay to be no shorter than 150 ms at <70 ppm.

Automatic AV delay initialization and automatic atrial sense latency compensation facilitates the management of the AV timing parameters while promoting native conduction in the CRM patient population.

These objectives are achieved by a heart stimulating system and a method that provides for automatic or device assisted initialization of AV delay values as follows:
  On implant detection, enable AV Hysteresis and collect 24-hr AV conduction statistics.
  If sufficient native sinus activity, configure the Atrial Sense Latency Compensation.
  If sufficient native AV conduction, customize the AV Delay and dynamics.
  If sufficient and acceptable AV conduction, enable AV Hysteresis.

Furthermore, the heart stimulation system and the method can provide follow-up recommendations as follows:
  Automatically review event counters and AV conduction statistics
  On user request recommend AV timing parameters.

It is to be appreciated that features of preferred embodiments of the invention may be combined in any useful manner thus arriving a further preferred embodiments of the invention not explicitly mentioned in this disclosure.

BRIEF DESCIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
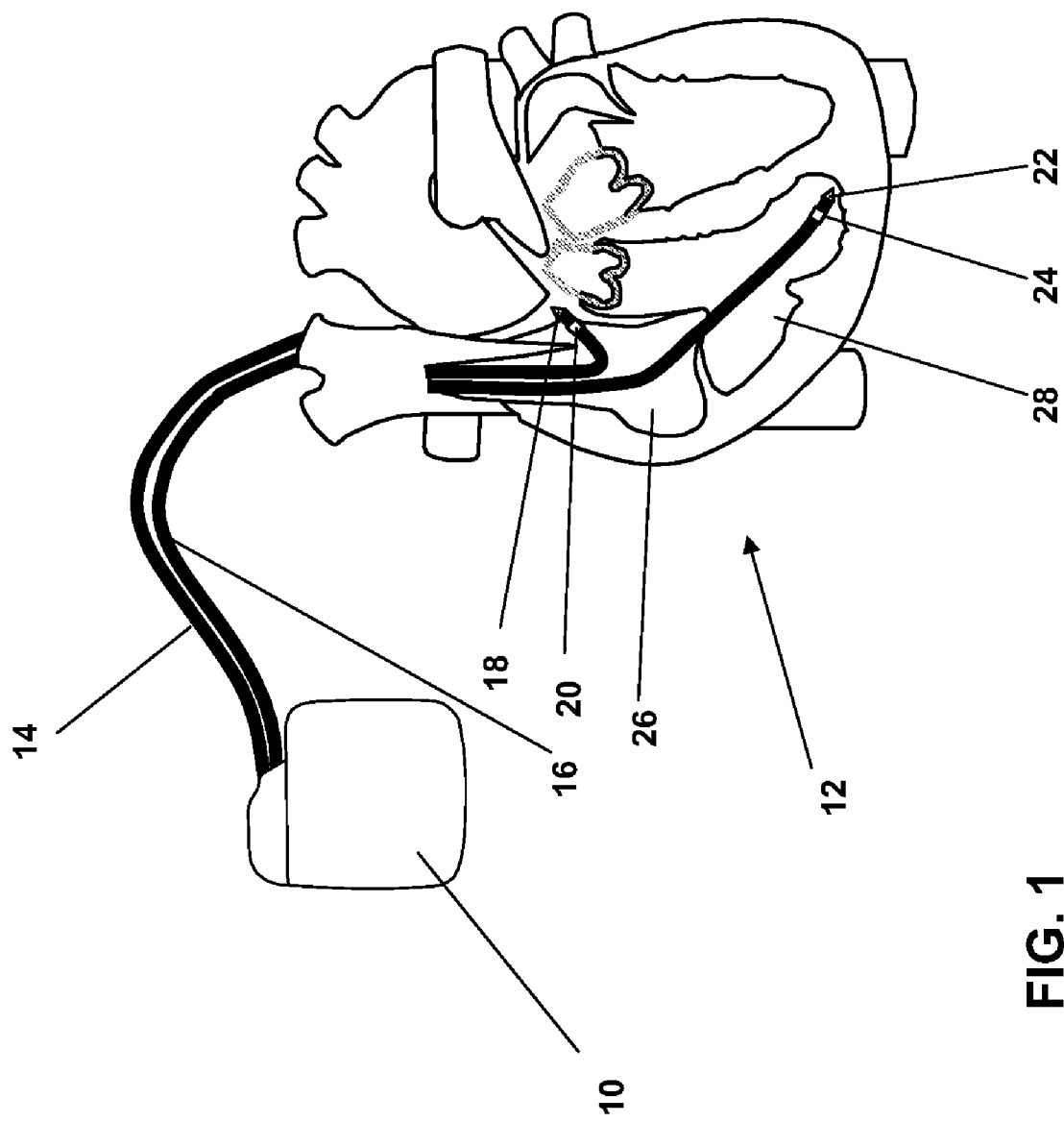
FIG. 1 shows a dual chamber pacemaker connected to leads placed in a heart.

In FIG. 1 a dual chamber pacemaker 10 as heart stimulator connected to pacing/sensing leads placed in a heart 12 is illustrated. The pacemaker 10 is electrically coupled to heart 12 by way of leads 14 and 16. Lead 14 has a pair of right atrial electrodes 18 and 20 that are in contact with the right atria 26 of the heart 12. Lead 16 has a pair of electrodes 22 and 24 that are in contact with the right ventricle 28 of heart 12. Electrodes 18 and 22 are tip-electrodes at the very distal end of leads 14 and 16, respectively. Electrode 18 is a right atrial tip electrode RA-Tip and electrode 22 is a right ventricular tip electrode RV-Tip 22. Electrodes 20 and 24 are ring electrodes in close proximity but electrically isolated from the respective tip electrodes 18 and 22. Electrode 20 forms a right atrial ring electrode RA-Ring and electrode 24 forms a right ventricular ring electrode RV-Ring.

Figure 2:
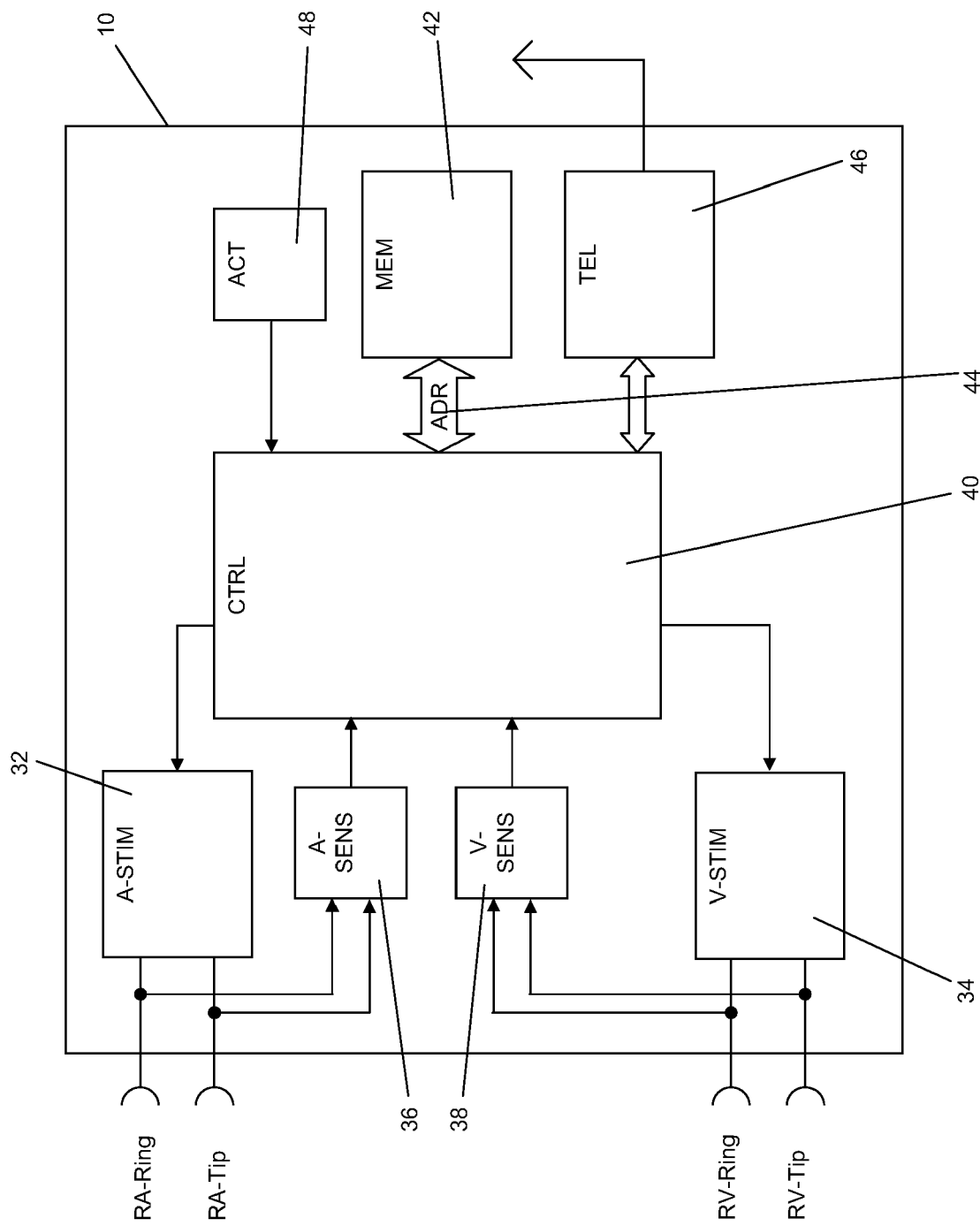
FIG. 2 is a block diagram of a heart stimulator according to the invention.

Referring to FIG. 2 a simplified block diagram of a dual chamber pacemaker 10 is illustrated. During operation of the pacemaker leads 14 and 16 are connected to respective output/input terminals of pacemaker 10 as indicated in FIG. 1 and carry stimulating pulses to the electrode pairs 18, 20 and 22, 24 from an atrial stimulation pulse generator A-STIM 32 and a ventricular pulse generator V-STIM 34, respectively. Further, electrical signals from the atrium are carried from the electrode pair 18 and 20, through the lead 14, to the input terminal of an atrial channel sensing stage A-SENS 36; and electrical signals from the ventricles are carried from the electrode pair 22 and 24, through the lead 16, to the input terminal of a ventricular sensing stage V-SENS 38.

Controlling the dual chamber pacer 10 is a control unit CTRL 40 that is connected to sensing stages A-SENS 36 and V-SENS 38 and to stimulation pulse generators A-STIM 32 and V-STIM 34. Control unit CTRL 40 receives the output signals from the atrial sensing stage A-SENS 36 and from the ventricular sensing stage V-SENS 38. The output signals of sensing stages A-SENS 36 and V-SENS 38 are generated each time that a P-wave representing an intrinsic atrial event or an R-wave representing an intrinsic ventricular event, respectively, is sensed within the heart 12. An As-signal is generated, when the atrial sensing stage A-SENS 36 detects a P-wave and a Vs-signal is generated, when the ventricular sensing stage V-SENS 38 detects an R-wave.

Control unit CTRL 40 also generates trigger signals that are sent to the atrial stimulation pulse generator A-STIM 32 and the ventricular stimulation pulse generator V-STIM 34, respectively. These trigger signals are generated each time that a stimulation pulse is to be generated by the respective pulse generator A-STIM 32 or V-STIM 34. The atrial trigger signal is referred to simply as the "A-pulse", and the ventricular trigger signal is referred to as the "V-pulse". During the time that either an atrial stimulation pulse or ventricular stimulation pulse is being delivered to the heart, the corresponding sensing stage, A-SENS 36 and/or V-SENS 38, is typically disabled by way of a blanking signal presented to these amplifiers from the control unit CTRL 40, respectively. This blanking action prevents the sensing stages A-SENS 36 and V-SENS 38 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Control unit CTRL 40 comprises circuitry for timing ventricular and/or atrial stimulation pulses according to an adequate stimulation rate that can be adapted to a patient's hemodynamic need as pointed out below.

Still referring to FIG. 2, the pacer 10 includes a memory circuit MEM 42 that is coupled to the control unit CTRL 40 over a suitable data/address bus ADR 44. This memory circuit MEM 42 allows certain control parameters, used by the control unit CTRL 40 in controlling the operation of the pacemaker 10, to be programmably stored and modified, as required, in order to customize the pacemaker's operation to suit the needs of a particular patient. Such data includes the basic timing intervals used during operation of the pacemaker 10 and AV delay values and hysteresis AV delay values in particular.

Further, data sensed during the operation of the pacemaker may be stored in the memory MEM 42 for later retrieval and analysis. This includes atrioventricular interval data that are acquired by the control unit CTRL 40. Control unit CTRL 40 is adapted to determine the atrioventricular interval data as required for automatic atrioventricular interval analysis by determining the time interval between an atrial event, either sensed (As) or stimulated (Ap) and an immediately following ventricular sensed event Vs as indicated by the ventricular sensing stage V-SENS 38.

A telemetry circuit TEL 46 is further included in the pacemaker 10. This telemetry circuit TEL 46 is connected to the control unit CTRL 40 by way of a suitable command/data bus. Telemetry circuit TEL 46 allows for wireless data exchange between the pacemaker 10 and some remote programming or analyzing device which can be part of a centralized service center serving multiple pacemakers.

The pacemaker 10 in FIG. 1 is referred to as a dual chamber pacemaker because it interfaces with both the right atrium 26 and the right ventricle 28 of the heart 12. Those portions of the pacemaker 10 that interface with the right atrium, e.g., the lead 14, the P-wave sensing stage A-SENSE 36, the atrial stimulation pulse generator A-STIM 32 and corresponding portions of the control unit CTRL 40, are commonly referred to as the atrial channel. Similarly, those portions of the pacemaker 10 that interface with the right ventricle 28, e.g., the lead 16, the R-wave sensing stage V-SENSE 38, the ventricular stimulation pulse generator V-STIM 34, and corresponding portions of the control unit CTRL 40, are commonly referred to as the ventricular channel.

In order to allow rate adaptive pacing in a DDDR or a DDIR mode, the pacemaker 10 further includes a physiological sensor ACT 48 that is connected to the control unit CTRL 40 of the pacemaker 10. While this sensor ACT 48 is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, blood pH, intra-cardiac impedance changes, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

The control unit CTRL 40 is adapted to determine an adequate heart rate or stimulation rate in any manner known as such. Furthermore, control unit CTRL 40 is adapted to apply AV delay values stored in an AV-delay value memory that is part of memory MEM 42 for atrium synchronous stimulation of the ventricle of the heart and—if applicable—a hysteresis AV delay.

With respect to AV-delay optimization, an atrioventricular interval timing analyzing unit is provided that is either a part of control unit CTRL 40 or that is connected to the control unit.

Atrioventricular Interval Data Collection:

The atrioventricular interval timing analyzing unit is adapted to accumulate instances of AV conduction intervals in the corresponding timing bins for the associated event sequences (AsVs or ApVs) and heart rate band.

The atrioventricular interval timing analyzing unit is adapted to classify atrioventricular intervals including AsVs and ApVs intervals that is intervals between an intrinsic atrial excitation As and an intrinsic ventricular excitation Vs and a stimulated atrial excitation Ap and an intrinsic ventricular excitation Vs, respectively. Atrioventricular timing information required for that evaluation is received from the control unit CTRL 40.

If a stable heart rhythm is present, the atrioventricular interval timing analyzing unit is adapted to sort all atrioventricular intervals into 10 histograms. A first group of histograms is set up for collecting AsVs intervals and a second group of histogram is set up for collecting ApVs intervals.

Both groups of histograms comprise 5 histograms each one being assigned to a different frequency band of heart rates, namely heart rates below 70 ppm, heart rates in the range from 70 to 89 ppm, heart rates in the range from 90 to 109 ppm, heart rates in the range from 110 to 129 ppm, and heart rates equal to or higher than 130 ppm.

Each histogram comprises 26 bins wherein each bin corresponds to a range in atrioventricular intervals. In a first bin a count of all the atrioventricular intervals shorter than 102 ms are accumulated. All further 25 bins cover a range of 7, 8 ms, see the table below:

| | | |
|---|---|---|
| 1$^{st}$ bin | | to <102 ms |
| 2$^{nd}$ bin | from | 102 ms to <109.8 ms |
| 3$^{rd}$ bin | from | 109.8 ms to <117.6 ms |
| 4$^{th}$ bin | from | 117.6 ms to <125.4 ms |
| 5$^{th}$ bin | from | 125.4 ms to <133.2 ms |
| 6$^{th}$ bin | from | 133.2 ms to <141 ms |
| 7$^{th}$ bin | from | 141 ms to <148.8 ms |
| 8$^{th}$ bin | from | 148.8 ms to <156.6 ms |
| 9$^{th}$ bin | from | 156.6 ms to <164.4 ms |
| 10$^{th}$ bin | from | 164.4 ms to <172.2 ms |
| 11$^{th}$ bin | from | 172.2 ms to <180 ms |
| 12$^{th}$ bin | from | 180 ms to <187.8 ms |
| 13$^{th}$ bin | from | 187.8 ms to <195.6 ms |
| 14$^{th}$ bin | from | 195.6 ms to <203.4 ms |
| 15$^{th}$ bin | from | 203.4 ms to <211.2 ms |
| 16$^{th}$ bin | from | 211.2 ms to <219 ms |
| 17$^{th}$ bin | from | 219 ms to <226.8 ms |
| 18$^{th}$ bin | from | 226.8 ms to <234.6 ms |
| 19$^{th}$ bin | from | 234.6 ms to <242.4 ms |
| 20$^{th}$ bin | from | 242.4 ms to <250.2 ms |
| 21$^{st}$ bin | from | 250.2 ms to <258 ms |
| 22$^{nd}$ bin | from | 258 ms to <265.8 ms |
| 23$^{rd}$ bin | from | 265.8 ms to <273.6 ms |
| 24$^{th}$ bin | from | 273.6 ms to <281.4 ms |
| 25$^{th}$ bin | from | 281.4 ms to <289.2 ms |
| 26$^{th}$ bin | from | 289.2 ms to <297 ms |

The width of the first AsVs bin, <102 ms, is 86 ms wide. The width of the first ApVs bin, <102 ms, is less than 7.8 ms wide, because the safety window usually triggers a ventricular pace at 100 ms and the device reclassifies the AV sequence as ApVp.

Atrioventricular Timing Analysis:

The atrioventricular interval timing analyzing unit is further adapted to determine whether or not a stable atrio-ventricular sequential rhythm is present for more than 75% of a predetermined time window that includes a plurality of heart cycles. Only if such stable heart rhythm is present, the determined atrioventricular intervals are evaluated or even accumulated in the histograms.

The atrioventricular interval timing analyzing unit is adapted to determine the presence of a stable heart rhythm by comparing the number of atrial events with the number of ventricular event in the predetermined time window. If the number of atrial events exceeds the number of ventricular events by more than 25%, no stable (that is, an instable) heart rhythm is determined. The atrioventricular interval timing analyzing unit is further adapted to determine the number of pairs of immediately consecutive ventricular events (that is pairs of ventricular events with no intermediate atrial event) and to compare that number to the number of ventricular events in the predetermined time window. If the number of pairs of immediately consecutive ventricular events exceeds 25% of the number of ventricular events in the predetermined time window no stable atrio-ventricular sequential rhythm is determined.

Furthermore, the atrioventricular interval timing analyzing unit is adapted to check for a presence of a third degree AV block. If the sum of all AsVs and ApVs events is less the 0.03 times the number of all AV events (including i.e. ApVp and AsVp events), no evaluation of atrioventricular intervals is performed.

In addition to the previous conditions, no evaluation of atrioventricular intervals is performed on an AV conduction histogram if the combined bins contain fewer than 100 counts.

Evaluation of the atrioventricular histograms is performed by the atrioventricular interval timing analysis unit as follows:

First, a distribution size is determined for each histogram. The distribution size is the sum of the counts in the bins from the second bin to the 26th bin, and thus excluding the shortest bin (<102 ms).

Preferably only those histograms are considered for further evaluation that have a distribution size of at least a quarter of the size of the histogram having the largest distribution size.

Then, for each histogram a median atrioventricular interval is determined. The median atrioventricular interval is the upper boundary of the interval-bin that includes the median atrioventricular interval. The median atrioventricular interval is determined by calculating the cumulative distribution from the atrioventricular conduction histogram. The median atrioventricular interval is equivalent to the upper boundary of the interval-bin for which the cumulative sum first exceeds half of the total distribution size.

In a similar manner, the atrioventricular interval timing analysis unit determines an upper limit for the atrioventricular conduction time. The upper limit atrioventricular interval is equivalent to the upper boundary of the interval-bin for which the cumulative sum first exceeds an upper-limit threshold. The count representing the upper-limit threshold is a specified fraction of the total counts, for example 97% of the total counts in the distribution.

The atrioventricular interval timing analysis unit further determines an atrial sense latency time. The atrial sense latency time is the difference in appropriate measures of the ApVs and AsVs distributions for a given heart rate frequency band. The appropriate measures include the median atrioventricular interval and the upper limit atrioventricular interval. The upper limit atrioventricular interval is used to calculate the atrial sense latency time because it is least distorted by rhythm artifacts and is consistent with preserving a native atrioventricular conduction.

Following the determination of the distribution size, the median atrioventricular interval, the upper limit atrioventricular interval and the atrial sense latency time, the atrioventricular interval timing analysis unit conducts an atrioventricular conduction analysis. The atrioventricular conduction analysis includes the determination of an upper ApVs conduction limit, an upper AsVs conduction limit, an average or median ApVs conduction interval, a average or median AsVs conduction interval, conduction dynamics for ApVs sequences, conduction dynamics for AsVs sequences and an average atrial latency time as follows:

Upper ApVs Conduction Limit:

The ApVs upper conduction limit is set to the longest of the upper-limit atrioventricular intervals obtained from the valid ApVs histogram distributions.

Upper AsVs Conduction Limit:

The AsVs upper conduction limit is set to the longest of the upper-limit atrioventricular intervals obtained from the valid AsVs histogram distributions.

Average ApVs Conduction Interval:

If two or more ApVs median intervals are available, the Significant Distributions are averaged. If a single ApVs median interval is available this ApVs median interval is used, otherwise, no measurement is made.

Average AsVs Conduction Interval:

If two or more AsVs median intervals are available, the Significant Distributions are averaged. If a single AsVs median interval is available AsVs median interval is used, otherwise, no measurement was made.

Conduction Dynamics for ApVs Sequences

If upper limit intervals are available for two or more ApVs rate bands, the conduction dynamics are calculated as the average conduction time difference per one positive step in the rate-band. The measured ApVs conduction dynamics is expressed in units milliseconds per beat per minute [ms/bpm]. The results are constrained to the range: −1.5 to 0.0 ms/bpm.

Conduction Dynamics for AsVs Sequences

If upper limit intervals are available for two or more AsVs rate bands; the conduction dynamics are calculated as the average conduction time difference per one positive step in the rate-band. The measured AsVs conduction dynamics is expressed in units of ms/bpm. The results are constrained to the range: −1.5 to 0.0 ms/bpm.

Average Atrial Latency Time

Average atrial latency time is determined for each heart rate band for which both the atrial-paced and atrial-sensed distributions are available. Atrial sense latency times are calculated as the ApVs upper-limit interval minus the AsVs upper-limit interval. Negative results are constrained to zero. The confidence in the latency measurement is based on the product of the number of counts in the paired distributions (ApVs counts*AsVs counts=confidence-product). The latency times having a confidence-product at least a quarter of the maximum confidence-product are averaged. The use of a quality measure with the latency measurements prevents infrequent timing events from distorting the average.

For automatic atrioventricular timing analysis the atrioventricular interval timing analyzing unit is adapted to perform a method that includes the following steps:

Accumulate and analyze atrioventricular intervals recorded over at least 24-hr, thereby using a long AV delay of 250 ms to 300 ms for ventricular stimulation.

Check for evidence of native (natural) atrioventricular conduction leading to intrinsic ventricular events Vs.

If no evidence of native AV conduction are found, in particular if less than 3% of all recorded ventricular events are intrinsic ventricular events, then program standard AV delay values into the AV delay memory and do not enable AV hysteresis If sufficient evidence of native AV conduction are found, in particular if equal to or more than 3% of all recorded ventricular events are intrinsic ventricular events, then determine a longer edge of the distribution of recorded atrioventricular intervals, e.g. the atrioventricular that forms the 97-th percentile of the recorded atrioventricular intervals, calculate the atrial latency time program the hysteresis AV delay to include the longer edge of the distribution of recorded atrioventricular intervals, e.g. the 97-th percentile interval, program a short ApVp delay as follows:

preserve the AV hysteresis timing as constrained by the device's AV hysteresis options target the short AV delay to be at least 30 ms shorter than the median ApVs interval constrain the AV delay to be no shorter than 150 ms at <70 ppm The $97^{th}$ percentile atrioventricular interval is determined in the same manner as the median atrioventricular interval or the upper limit atrioventricular interval: The $97^{th}$ percentile atrioventricular interval is determined to be the atrioventricular interval that is assigned to the interval bin, which includes the atrioventricular interval sample for which at least 3% of all atrioventricular samples are longer. The $97^{th}$ percentile atrioventricular interval is determined by summing the counts from the longest interval towards the shortest interval bin. The atrioventricular interval sample associated with the addition operation, which first causes the sum to exceed 3% of the total number of counts (the distribution size) is designated the upper limit atrioventricular interval.

Parameter Selection for Atrioventricular Timing:

With respect to programming an adequate AV delay and an adequate hysteresis AV delay for AV-sequential stimulation (atrium synchronous stimulation), the control unit and the memory of the heart stimulator are adapted as follows:

If no automatic setting is available:

If insufficient AV native AV conduction is observed, then standard AV timing parameters are used for AV delay. The latency compensation is programmed to the standard value. AV hysteresis is programmed "Off".

Otherwise, if sufficient native atrioventricular conduction is observed and thus sufficient atrioventricular interval data was recorded, automatic timing parameter adjustment is performed by the control unit and the atrioventricular interval timing analyzing unit:

Automatic Latency Compensation

The latency compensation is a negative valued programmable parameter. The corrected atrial latency should remain positive, and not be over corrected. The most negative value for latency compensation shall be selected, which obeys the following relationship:

atrial latency+latency compensation≧zero

Contingencies for automatic latency compensation are:

If the atrial latency is invalid, then the latency compensation is programmed to the standard value.

If the atrial latency is zero or negative, then the latency compensation is programmed to Off.

Automatic AV Hysteresis (Long ApVp Delay)

Preference is given to permitting native AV sequential stimulation. The hysteresis AV delay is selected which is greater or equal to the longest upper limit atrioventricular interval for the significant distributions:

Hysteresis AV delay≧upper ApVs conduction limit and

Hysteresis *AV* delay≧(upper *AsVs* conduction limit− latency compensation)

Automatic AV Delay (Short ApVp Delay)

The ApVp delay is selected to approach the optimal hemodynamic performance for pacing therapy. If the patient's optimal ApVp interval has been independently determined, it shall provide the preferred targeted ApVp interval. In the absence of a patient specific optimal ApVp interval, the targeted ApVp interval is estimated based on the median ApVs interval minus 30 ms. Since the putative ApVp interval may be biased by the clinical condition of the patient, the programmed value is constrained by the lower limit of the published range for optimal ApVp intervals: 160±20 ms. The constrained ApVp interval is the targeted ApVp delay.

Contingency for Automatic AV Delay:

If the targeted ApVp delay cannot be programmed due to limited programming options, the nearest available ApVp delay shall be used.

Although an exemplary embodiment of the present invention has been shown and described, it should be apparent to those of ordinary skill that a number of changes and modifications to the invention may be made without departing from the spirit and scope of the invention. For example, the principles of atrioventricular interval analysis and the principles of automatic or device-assisted semi-automatic AV-delay adjustment can be applied to dual or more chamber heart stimulators including ICDs. Furthermore, all features illustrated above can be integrated into an implantable medical device itself. However, it is also possible to have only parts of the heart stimulation system that are needed for daily operation of the implant are integrated in the implant while other parts such as the atrioventricular interval timing analyzing unit can be implemented into an external device that is remotely connected to the implant. This invention can readily be adapted to such devices by following the present teachings. All such changes, modifications and alterations should therefore be recognized as falling within the scope of the present invention.

What is claimed is:

1. A heart stimulating system for stimulating at least a ventricle of a heart comprising:
   a stimulation pulse generator configured to generate electric stimulation pulses and being connected or being connectable to at least a ventricular stimulation electrode configured to deliver electric stimulation pulses to at least a ventricle of a heart;
   an atrial sensing stage connected or being connectable to an electrode configured to pick up electric potentials inside at least an atrium of said heart, said atrial sensing stage configured to sense an excitation or a contraction of atrial myocardium;
   a ventricular sensing stage connected or being connectable to a second electrode configured to pick up electric potentials inside at least a ventricle of said heart, said ventricular sensing stage configured to sense an excitation or a contraction of ventricular myocardium;
   a memory configured to store AV-delay values;
   a control unit that is connected to said memory, at least one sensing stage and to said stimulation pulse generator, said control unit configured to trigger said stimulation pulse generator to generate ventricular stimulation pulses that are timed based on said AV-delay values stored in said memory and to acquire atrioventricular interval samples that represent time interval AsVs or ApVs between an atrial sense event As or an atrial stimulation pulse Ap, respectively, and a subsequent ventricular sense event;
   an atrioventricular interval timing analyzing unit that is part of said control unit or that is connected to said control unit wherein said atrioventricular interval timing analyzing unit is configured to receive atrioventricular interval samples from said control unit wherein said atrioventricular interval timing analyzing unit is further configured to generate at least one histogram based on said atrioventricular interval samples received from said control unit and analyze said at least one histogram to determine a $m^{th}$ q-quantile atrioventricular interval based on counts in said at least one histogram with $0<m<q$;
   wherein said atrioventricular interval timing analyzing unit is further configured to
      accumulate and analyze atrioventricular intervals recorded over at least 24-hr, while a long AV delay of 250 ms to 300 ms for ventricular stimulation is utilized;
      check for evidence of native or natural atrioventricular conduction leading to intrinsic ventricular events Vs wherein
         if no evidence of native AV conduction are found, then store AV delay values into an AV delay memory and without enablement of AV hysteresis and
         if sufficient evidence of native AV conduction are found, then
            determine a longer edge of a distribution of recorded atrioventricular intervals, and determine a AV delay that corresponds to a desired high percentile of recorded atrioventricular intervals greater than a median value;
            calculate atrial latency time
            set a hysteresis AV delay to said AV delay that corresponds to said desired high percentile of recorded atrioventricular intervals.

2. The heart stimulating system according to claim 1, wherein said atrioventricular interval timing analyzing unit is further configured to:
   generate a plurality of histograms based on said atrioventricular interval samples received from said control unit, wherein each histogram is assigned to a different range of heart rates or stimulation rates; and,
   analyze said plurality of histograms to determine a plurality of $m^{th}$ q-quantile atrioventricular intervals based on counts in said plurality of histograms with $0<m<q$.

3. The heart stimulating system according to claim 1, wherein said atrioventricular interval timing analyzing unit is further configured to generate one or more AV-delay values that depends on said $m^{th}$ q-quantile atrioventricular interval or intervals, respectively.

4. The heart stimulating system according to claim 3, wherein said atrioventricular interval timing analyzing unit is further configured to analyze said at least one histogram to determine a median atrioventricular interval based on counts in said at least one histogram.

5. The heart stimulating system according to claim 4, wherein said atrioventricular interval timing analyzing unit is further configured to generate said one or more AV-delay values that depend on said one or more of said median atrioventricular interval.

6. The heart stimulating system according to claim 5, wherein said atrioventricular interval timing analyzing unit is further configured to generate said one or more AV-delay values so as to correspond to a respective one or more median atrioventricular interval minus a predetermined time interval.

7. The heart stimulating system according to claim 6, wherein said predetermined time interval has a duration of at least 30 ms or is up to 40 ms.

8. The heart stimulating system according to claim 3, wherein said atrioventricular interval timing analyzing unit is further configured to analyze said at least one histogram to determine one or more upper limit atrioventricular intervals based on counts in said at least one histogram.

9. The heart stimulating system according to claim 8, wherein an upper limit atrioventricular interval corresponds to a $97^{th}$ percentile atrioventricular interval for a respective range of heart rates or stimulation rates.

10. The heart stimulating system according to claim 8, wherein said atrioventricular interval timing analyzing unit is further configured to generate one or more AV hysteresis interval values that depends on said one or more upper limit atrioventricular intervals.

11. The heart stimulating system according to claim 1, wherein said atrioventricular interval timing analyzing unit is further configured to analyze said at least one histogram to determine an atrial latency time based on said counts in said at least one histogram.

12. The heart stimulating system according to claim 1, wherein said atrioventricular interval timing analysis unit is further configured to determine an $m^{th}$ q-quantile, which includes a atrioventricular interval sample for which at least m/q of all atrioventricular samples are shorter.

13. The heart stimulating system according to claim 12, wherein said atrioventricular interval timing analyzing unit is further configured to determine said $m^{th}$ quantile atrioventricular interval via a sum of counts from a longest interval towards a shortest interval and to designate said $m^{th}$ q-quantile atrioventricular interval to be said atrioventricular interval sample associated with an addition operation, which first causes a sum to exceed m/q of a total number of atrioventricular interval samples.

14. The heart stimulating system according to claim 1, wherein said stimulation pulse generators, said sensing stages and said control unit are arranged within a housing of an implantable medical device whereas said atrioventricular interval timing analyzing unit is part of an external device, said implantable medical device and said external device each comprising a transceiver that is connected to said control unit and to said atrioventricular interval timing analyzing unit, respectively, such that a bidirectional data communication between said control unit and said atrioventricular interval timing analyzing unit can be established.

15. The heart stimulating system according to claim 1, wherein said stimulation pulse generators, said sensing stages, said control unit and said atrioventricular interval timing analyzing unit are arranged within a housing of an implantable medical device.

16. The heart stimulating system according to claim 1, wherein said atrioventricular interval timing analyzing unit is further configured to:
confirm sufficient atrioventricular conduction prior to generation of an AV delay value or an hysteresis AV delay value; and,
not generate said AV delay value or said hysteresis AV delay value if no sufficient atrioventricular conduction is confirmed.

17. The heart stimulating system according to claim 1, wherein said atrioventricular interval timing analyzing unit is further configured to confirm sufficient atrioventricular conduction through comparison of a number of intrinsic ventricular events Vs to a number of stimulated ventricular events Vp within a predetermined time window.

18. The heart stimulating system according to claim 17, wherein said atrioventricular interval timing analyzing unit is further configured to confirm sufficient atrioventricular conduction if at least a minimal fraction of all ventricular events are intrinsic events.

19. The heart stimulating system according to claim 1, wherein said atrioventricular interval timing analyzing unit is further configured to:
generate an hysteresis AV delay value that corresponds to an $m^{th}$ q-quantile atrioventricular interval with m being equal to or larger than 95% of q.

20. The heart stimulating system according to claim 1, wherein said atrioventricular interval timing analyzing unit is further configured to:
set a short ApVp delay so as to
utilize AV hysteresis timing as constrained by AV hysteresis options;
set a short AV delay to be at least 30 ms shorter than a median ApVs interval; and,
constrain an AV delay to be no shorter than 150 ms at heart rates less than 70 ppm.

21. The heart stimulating system according to claim 1, wherein said atrioventricular interval timing analyzing unit is further configured to:
determine that no evidence of native AV conduction is found if less than 3% of all recorded ventricular events are intrinsic ventricular events.

22. The heart stimulating system according to claim 1, wherein said atrioventricular interval timing analyzing unit is further configured to:
determine that sufficient evidence of native AV conduction is found if equal to or more than 3% of all recorded ventricular events are intrinsic ventricular events.

23. The heart stimulating system according to claim 1, wherein said atrioventricular interval timing analyzing unit is further configured to:
determine that no evidence of native AV conduction is found if less than 3% of all recorded ventricular events are intrinsic ventricular events; and,
determine that sufficient evidence of native AV conduction is found if equal to or more than 3% of all recorded ventricular events are intrinsic ventricular events.

* * * * *